United States Patent [19]

Jaw

[11] Patent Number: 4,502,469
[45] Date of Patent: Mar. 5, 1985

[54] MILD-TEMPERATURE THERMOMASSAGE INSTRUMENT

[76] Inventor: Jih-long Jaw, 105 Ta-Tung South St., Son-Ho Li, Nan-Tou Town, Nan-Tou Hsien, Taiwan

[21] Appl. No.: 402,144

[22] Filed: Jul. 26, 1982

[51] Int. Cl.³ .............................................. A61H 29/00
[52] U.S. Cl. .................................................... 128/24.1
[58] Field of Search ...................... 128/24.1, 362, 783, 128/784; 338/302, 303, 305, 296, 270, 267, 268

[56] References Cited

U.S. PATENT DOCUMENTS

| | | | |
|---|---|---|---|
| 1,384,067 | 7/1921 | Hynes | 338/305 X |
| 1,638,829 | 8/1927 | Colby | 338/303 X |
| 1,690,926 | 11/1928 | Dequer | 128/24.1 |
| 2,280,367 | 4/1942 | Barton | 338/303 X |
| 2,488,591 | 11/1949 | Fevas | 128/24.1 |
| 2,638,527 | 5/1953 | Curtis | 128/24.1 |
| 2,739,586 | 3/1956 | Preis | 128/24.1 |
| 2,929,374 | 3/1960 | O'Gara | 128/24.1 |

FOREIGN PATENT DOCUMENTS

| | | | |
|---|---|---|---|
| 815315 | 6/1969 | Canada | 128/24.1 |

Primary Examiner—Steven A. Bratlie
Assistant Examiner—David J. Brown
Attorney, Agent, or Firm—McGlew and Tuttle

[57] ABSTRACT

A mild-temperature thermomassage instrument comprises substantially a hollow and truncated oval body made of Bakelite material and a hollow elliptic front head of aluminum. The truncated oval body includes a lower housing and an upper housing with a wiring plate having a button switch and power lines provided thereto being installed in the lower housing. A heating element, which comprises a refractory core rod with an electric resistance wire wound around the outer surface and mica material wrapped thereon, and a thin and grilled copper thimble covered around the finished core rod and secured thereto, is positioned in a closed space formed within the hollow section of the elliptic front head coupled with the truncated oval body at one end through a Bakelite lining ring, so that, by the special oval structure and the mild-temperature function, this instrument is very suitable for hand manipulation in applying hot compress and thermal massage on all parts of the human body.

9 Claims, 2 Drawing Figures

MILD-TEMPERATURE THERMOMASSAGE INSTRUMENT

BACKGROUND OF THE INVENTION

This invention relates to a mild-temperature thermomassage instrument, which is particularly suitable for hand manipulation in applying hot compress and thermal massage upon the human body.

It is understood that various kinds of electric massage instrument are available at present. However, none of the known electric massage instruments is applicable to hot compress as well as massage because all of them are operated by an electric motor with very little variation of vibration. Therefore, up to the present time, no one kind of the conventional electric massage instruments can be suitable for applying massage on all parts of the human body.

On the other hand, although the conventional electric massage instrument is, in some way, effective in stimulating blood circulation and alleviating muscle fatigue, its efficiency is not satisfactory for individual requirements because of the monotonous vibration thereof.

SUMMARY OF THE INVENTION

It is accordingly a primary object of this invention to provide a mild-temperature thermomassage instrument with a novel structure for applying hot compress and thermal massage upon all parts of the human body through manual manipulation.

With this object in view, a mild-temperature thermomassage instrument according to this invention comprises a hollow and truncated oval body made of Bakelite material and coupled with a hollow elliptic front head of aluminium. The Bakelite oval body includes a lower housing and an upper housing, and a wiring plate assocated with a button switch and power lines provided thereto are installed therein. A heating element comprising a hollow refractory core rod with an electric resistance wire wound around the core rod and a sheet of mica wrapped around the outer surface thereof, and a thin and grilled thimble of copper covered the finished core rod and secured thereto, is positioned in a closed space formed within the hollow section of the elliptic front head, which is coupled with the oval body at the truncated end through a Bakelite lining ring thereof, so that, by the special oval structure and the mild-temperature function, this invention is very suitable for hand manipulation in applying hot compress and thermal massage upon all parts of the human body.

Other objects and advantages of this invention will become apparent to those skilled in the art from the following detailed description of a preferred embodiment when read in connection with the accompanying drawings.

DETAILED DESCRIPTION OF THE PREFERRED EMBODIMENT

Figure 1:
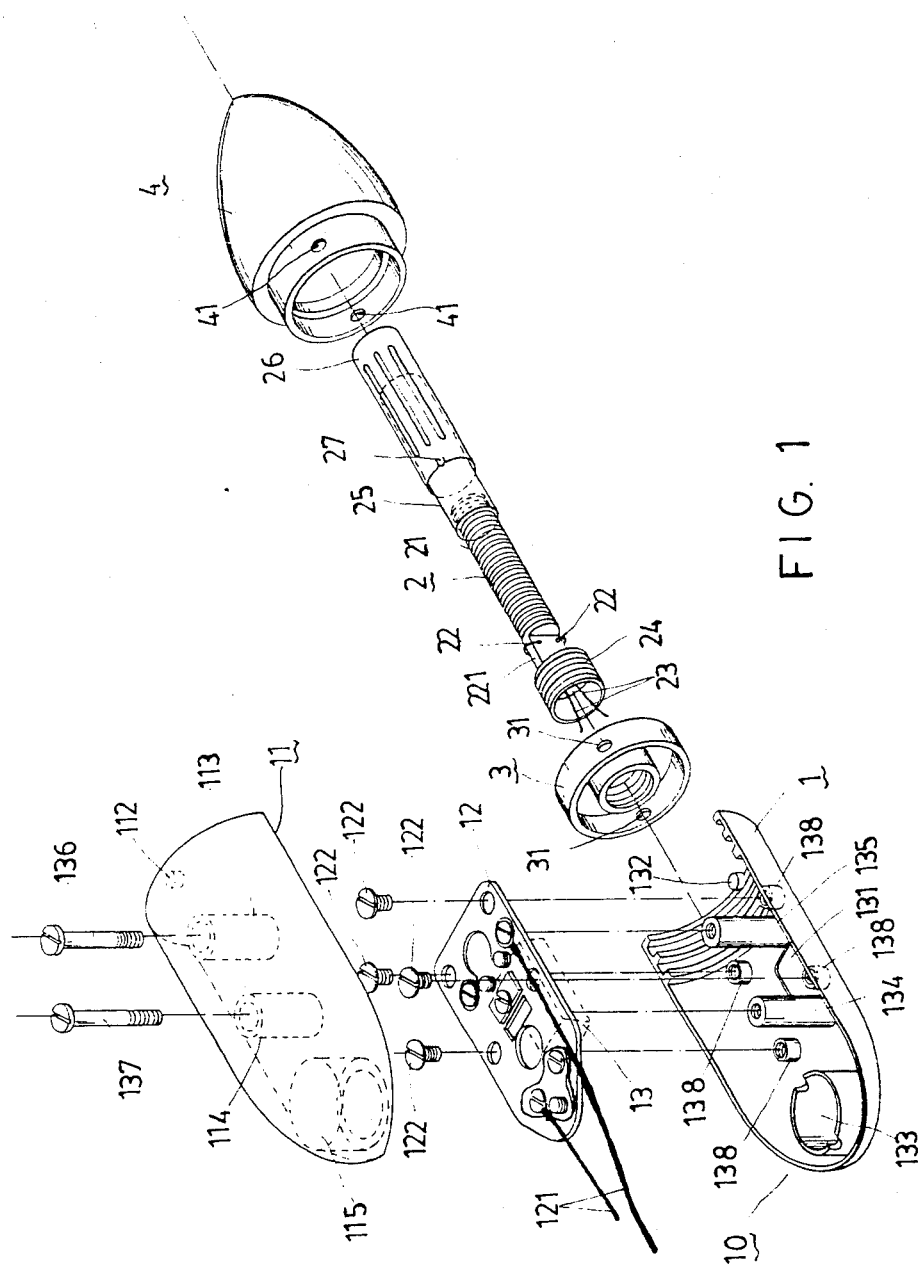
FIG. 1 is an exploded and perspective view of a mild-temperature thermomassage instrument embodying this invention.

Referring to FIG. 1, a preferred embodiment of a mild-temperature thermomassage instrument according to this invention comprises a hollow and truncated oval body 10 made of Bakelite material (which is heat resistant and insulating) and including a lower housing 1 having a plurality of tap holes 138 and a pair of studs 134, 135 integrally formed therein, and an upper housing 11 with a pair of coupling studs 113, 114 integrally provided therein. A wiring plate 12 with a plurality of binding screws provided thereto is fixed in the hollow section of the lower housing 1 through a plurality of screws 122 respectively secured to the tap holes 138 thereof with a button switch 13 electrically connected thereto and protruding out of a notch 131 formed at the edge of the lower housing 1. A pair of insulated electric wires 121 are separately connected to the wiring plate 12 with respect to the button switch 13. A refractory core rod 2 has a through opening in the middle, a helical groove around the surface, a flat portion at one end with an orifice 22 opposingly located at both rear sides thereof, a catch hole 221 provided at the front side, and a hollow screw base 24 integrally formed at the front end. An electric resistance wire 21 is wound around the core rod 2 by inserting one end of the resistance wire 21 from the rear end of the core rod 2 into the through opening thereof and extending to the flat portion of the front end with the wire end secured in one of the orifices 22 thereof, winding the remaining portion of the resistance 21 along the helical groove of the core rod 2 and securing the wire end in another one of the orifices 22 thereof, and then making electrical connections with a pair of insulated wires 23 respectively linked to the ends of the resistance wire 21 through the hollow section of the screw base 24 while the other ends of the wire 23 are terminated at the wiring plate 12. A sheet of mica material 25 is wrapped around the outer surface of the core rod 2 including the rear end and the orifices 22 before covering the sheet 25 with a thin and grilled copper thimble 26 over the finished core rod 2 by securing a locking catch 27 provided at one end of the copper thimble 26 at the catch hole 221 thereof, so that, a well isolated heating element is formed therewith. A mounting member in the form of an inner lining ring 3 made of lagging material, such as Bakelite, with a plurality of lock holes 31 formed in the peripheral surface and a threaded opening in the middle is coupled with the screw base 24 of the core rod 2 through the threaded opening thereof. A hollow and truncated elliptic front head 4, which is made of aluminium with a plurality of lock holes 41 formed in an extended rim along the inner edge of the truncated end, is coupled with the inner lining ring 3 and connected to the open end of the lower housing 1 and the upper housing 11 by respectively engaging the aligned lock holes 41 and 31 with the coupling stubs 112 and 132 thereof, so that a closed space is formed within the hollow section of the elliptic front head 4 with the heating element isolately located therein. The power line 121 is firmly kept in an annular recess 115 and 133 separately formed in the lower housing 1 and the upper housing 11, both of which are fixed by a pair of screw bolts 136, 137 respectively through the coupling studs 113, 114 and the studs 134, 135 thereof.

It will be appreciated that the instrument according to this invention features in the arrangement of the heating element within the hollow section of the elliptic front head 4 because the closed space formed between the finished core rod 2 and the inner wall (which has a certain thickness) provides a desirable area for heat transfer. As a result, the temperature produced by the electric resistance wire 21, which is isolated by the mica material 25, will be grandually transfered to the outer surface of the aluminium front head 4 through the closed space thereof and the wall thickness of the front head 4, so that a mild temperature can be maintained thereat under the control of the button switch 13. In addition, after the power is off, the dissipation of the heat produced therein is very slow because the closed space thereof and wall thickness of the front head 4 provide a good heat keeping effect therewith.

Figure 2:
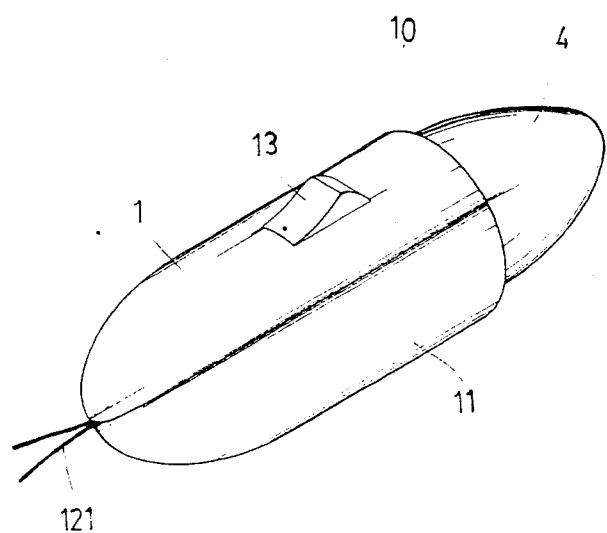
FIG. 2 is an isometric view of the preferred embodiment of FIG. 1 in assembled condition.

Shown in FIG. 2 is an isometric view of the embodiment of FIG. 1 in a complete assembly condition, wherein the oval end of the front head 4 extends out of the truncated end of the oval body 10, making the instrument a complete oval shape suitable for being held by hand in applying hot compress and thermal massage on all parts of the human body.

It will also be appreciated that the front edge of the truncated oval body 10 is higher than the circumscribed surface of the elliptic front head 4 so that the chance of contacting the warm surface of the front head 4 by the holding hand of the user is minimized accordingly. On the other hard, as the coupling between the front head 4 and the oval body 10 is made through the inner lining ring 3 and the coupling stubs 112, 132 (as shown in FIG. 1), the heat of the front head 4 will not be transferred to the oval body 10 so that the holding hand of the user will not feel the warm condition thereby.

While a preferred embodiment has been chosen to illustrate the invention, it will be understood by those skilled in the art that various changes and modifications can be made therein without departing from the scope of the invention as defined in the appended claims.

I claim:

1. A mild-temperature thermomassage instrument comprising:
   a hollow and truncated elongated oval body made of heat resistant and insulating material, having an open truncated end;
   a flat wiring plate made of heat resistant and insulating material disposed in said body;
   a pair of powerlines connected to said plate;
   button switch means engaged with said plate and said powerlines and movable in said body for supplying heating power;
   a hollow and truncated eliptical front head made of metal, defining an inner space and having an open truncated end connected to said open truncated end of said body;
   a rod shaped heating device extending into said inner space and spaced inwardly from said head, said heating device being electrically connected to said button means for receiving heating power for heating said inner space and said head;
   a mounting member made of heat resistant and insulating material connected to said body and to one end of said rod shaped heating device for supporting said rod shaped heating device in said inner space of said head;
   said heating device comprising a refractory core rod having a through opening in the middle thereof, a helical groove formed around an outer surface thereof, a flat portion extending at said one end of said rod shaped heating device with a pair of orifices in said flat portion, a hollow screw base connected to said flat portion and engageable with said mounting member for supporting said heating device, an electric resistance wire wound along said helical groove with opposite ends of said wire secured in each of said orifices respectively, a pair of insulated wires electrically connected to each of said ends of said electric resistance wire and extending through said hollow screw base, said two insulated wires connected to said button switch means and said powerlines for supplying power to said electric resistance wire, a sheet of mica material wrapped around an outer surface of said core rod with said electric resistance wire thereon, said sheet of mica material extending over said flat portion, a thin and grilled metal thimble extending over said sheet of mica material.

2. An instrument according to claim 1 wherein said mounting member comprises an inner lining ring having a central internally threaded portion threadably engaged with said hollow screw base of said heating device, with a plurality of holes in a peripheral surface of said inner lining ring, said hollow and truncated elongated body including a plurality of projections equal in number to said plurality of holes in said inner lining ring and engaged in each hole of said inner lining ring for securing said inner lining ring to said body.

3. An instrument according to claim 2 wherein said hollow and truncated eliptical front head includes a rim extending from said open truncated end of said head having a plurality of holes therein equal in number to said plurality of holes in said inner lining ring, said projections of said body respectively extending into said holes of said rim for securing said head to said body.

4. An instrument according to claim 3 wherein said body comprises an upper shell half and a lower shell half, said flat wiring plate connected between said upper and lower shell halves and each of said shell halves including at least one of said projections.

5. An instrument according to claim 4 wherein an outer diameter of said body is greater than an outer diameter of said head.

6. A mild-temperature thermomassage instrument comprising:
   a hollow and truncated elongated oval body made of heat resistant and insulating material, having an open truncated end;
   a flat wiring plate made of heat resistant and insulating material disposed in said body;
   a pair of powerlines connected to said plate;
   button switch means engaged with said plate and said powerlines and movable in said body for supplying heating power;
   a hollow and truncated eliptical front head made of metal, defining an inner space and having an open truncated end connected to said open truncated end of said body;
   a rod shaped heating device extending into said inner space and spaced inwardly from said head, said heating device being electrically connected to said button means for receiving heating power for heating said inner space and said head;
   a mounting member made of heat resistant and insulating material connected to said body and to one end of said rod shaped heating device for supporting said rod shaped heating device in said inner space of said head;
   said rod shaped heating device including a refractory core rod having a hollow screw base at said one end thereof, an electric resistance wire wound on said refractory core rod having connecting wires extending through said hollow screw base for connection to said button switch means and powerlines, said mounting member comprising a ring having an inner threaded portion threadably engaged with said hollow screw base and an outer portion with a plurality of peripheral openings, said hollow and truncated elongated oval body having a plurality of projections equal in number to said plurality of holes in said ring and extending respectively into said plurality of holes in said ring for securing said ring in said head.

7. An instrument according to claim 6 including a mica sleeve over said refractory core rod and electric resistance wire, and a metal sleeve over said mica sleeve.

8. An instrument according to claim 7 wherein said head includes a rim extending from said open truncated end of said head having a reduced diameter, said rim having a plurality of openings each engaged by one of said projections of said body for securing said head to said body.

9. An instrument according to claim 8 wherein an outer diameter of said body is greater than an outer diameter of said head.

* * * * *